US005693335A

United States Patent [19]
Xia et al.

[11] Patent Number: 5,693,335
[45] Date of Patent: Dec. 2, 1997

[54] SKIN PERMEATION ENHANCER COMPOSITION FOR USE WITH SEX STEROIDS

[75] Inventors: Jun Xia, Edison, N.J.; Janan Jona, Sunnyvale; Chia-Ming Chiang, Foster City, both of Calif.

[73] Assignee: Cygnus, Inc., Redwood City, Calif.

[21] Appl. No.: 472,810

[22] Filed: Jun. 7, 1995

[51] Int. Cl.⁶ .................................. A61F 13/02
[52] U.S. Cl. .................. 424/448; 424/449; 514/946
[58] Field of Search .................. 424/448, 449; 514/946

[56] References Cited

U.S. PATENT DOCUMENTS

| | | | |
|---|---|---|---|
| 4,195,095 | 3/1980 | Sheffner | 424/317 |
| 4,637,930 | 1/1987 | Konno et al. | 424/28 |
| 4,690,683 | 9/1987 | Chien | 604/896 |
| 5,053,227 | 10/1991 | Chiang et al. | 424/448 |
| 5,252,334 | 10/1993 | Chiang et al. | 424/448 |

FOREIGN PATENT DOCUMENTS

| | | |
|---|---|---|
| 2 141 025 | 12/1984 | United Kingdom . |
| 2 142 237 | 1/1985 | United Kingdom . |
| 2142238 | 1/1985 | United Kingdom . |

OTHER PUBLICATIONS

MTM Research Chemicals, Lancaster Catalogue, pp. 836 and 1206, 1991/92.

*Primary Examiner*—D. Gabrielle Phelan
*Attorney, Agent, or Firm*—Morrison & Foerster LLP

[57] ABSTRACT

A combination permeation enhancer for increasing the permeability of skin to sex steroids such as estrogens and progestogens comprising a polyhydric thioalcohol of 2 to 6 carbon atoms having at least one mercapto group and at least one hydroxy group and an aliphatic carboxylic acid of 8 to 24 carbon atoms or an ester thereof.

14 Claims, No Drawings

SKIN PERMEATION ENHANCER COMPOSITION FOR USE WITH SEX STEROIDS

DESCRIPTION

1. Technical Field

The invention is in the field of transdermal drug delivery. More particularly, it concerns a skin permeation enhancer composition for increasing the permeability of skin to sex steroids.

2. Background

Transdermal patches for administering drugs, including steroids, are well known. Transdermal patches include a component, typically called the "reservoir," that holds the bulk of the drug to be administered. One type of patch uses a solid matrix composed of a mixture of a pressure sensitive adhesive and the drug as the reservoir. The matrix also serves as the means for attaching the patch to the skin. Such patches are often referred to as "matrix" or "monolith" type patches.

Some drugs permeate unassisted through skin at rates that make it feasible to administer therapeutic amounts of the drug via a reasonably sized patch. For drugs that do not permeate through skin at such rates, it may be possible to increase the permeability of the skin to the drug with a permeation enhancer. For instance, most steroids require the use of a permeation enhancer to make transdermal administration feasible.

Numerous compounds and combinations of compounds have been used as permeation enhancers. Commonly owned U.S. Pat. No. 5,053,227, which is directed to using particular combinations of esters and ethers as permeation enhancers, describes many known enhancers in its "Description of the Prior Art" section.

The present invention concerns a combination of a polyhydric thioalcohol and an aliphatic carboxylic acid or ester thereof that is useful in a matrix type patch for administering sex hormones (estrogens, progestogens, and androgens).

U.S. Pat. No. 4,637,930 describes permeation enhancers for nicardipine hydrochloride. The enhancer is described as being "at least one of" ... thioglycerol, glycerides of $C_6$–$C_{12}$ fatty acids, and sorbitol esters of $C_6$–$C_{12}$ fatty acids. No examples of a combination of thioglycerol with another compound are described. Matrix type patches are not disclosed.

G.B. 2,142,238A teaches permeation enhancers composed of: (a) an adjuvant, (b) a solvent, and (c) a moderator. Among the adjuvants described are esters of $C_6$–$C_{16}$ fatty acids. Thioglycerol is among the solvents listed in the patent. The moderator is a diol. No specific combination of thioglycerol with any adjuvant/moderator is taught. The patent says the tertiary combination can be used to enhance the permeation of numerous drugs through skin and indicates the drug and enhancer can be incorporated into the adhesive base of an adhesive tape.

DISCLOSURE OF THE INVENTION

One aspect of the invention is a matrix for use in administering sex steroids transdermally comprising a mixture of:

a) a pressure-sensitive adhesive;

b) a sex steroid; and c) a skin permeation enhancer comprising a mixture of:
   (i) a polyhydric thioalcohol of 2 to 6 carbon atoms having at least one mercapto group and at least one hydroxy group; and
   (ii) an aliphatic carboxylic acid of 8 to 24 carbon atoms or an ester of said acid.

Another aspect of the invention is a transdermal patch for administering a sex steroid comprising a laminated composite of:

a) a backing layer; and b) a layer of the above described matrix underlying the backing layer.

MODES FOR CARRYING OUT THE INVENTION

As used herein to describe the thioalcohol component of the enhancer, the term "polyhydric" intends an alcohol having at least one mercapto (—SH) group and at least one hydroxy (—OH) group.

The sex steroids with which the combination enhancer of the invention is used include estrogens, progestogens, androgens, or any combination thereof. The steroid may be naturally occurring or synthetic. Examples of sex steroids are progesterone, norethindrone, norethindrone acetate, desogestrel, 3-ketodesogestrel, levonorgestrel, 17-deacetylnorgestimate, estradiol, estradiol valerate, estradiol cypionate, ethinyl estradiol, testosterone and its esters such as testosterone dienanthate. The steroid will normally constitute 0.1 to 20% by weight, more usually 0.2 to 6.0% by weight, of the matrix.

The pressure-sensitive adhesive will normally be a solution polyacrylate, a silicone, a polyisobutylene or a styrene-butadiene copolymer. Such adhesives are well known in the transdermal art. See, for instance, the Handbook of Pressure Sensitive Adhesive Technology, 2nd Edition (1989) Van Nostrand, Reinhold.

Pressure sensitive solution polyacrylate adhesives are made by copolymerizing one or more acrylate monomers ("acrylate" is intended to include both acrylates and methacrylates), one or more modifying monomers, and one or more functional group-containing monomers in an organic solvent. The acrylate monomers used to make these polymers are normally alkyl acrylates of 4–17 carbon atoms, with 2-ethylhexyl acrylate, butyl acrylate, and isooctyl acrylate being preferred. Modifying monomers are typically included to lower the $T_g$ of the polymer. Such monomers as vinyl acetate, ethyl acrylate and methacrylate, and methyl methacrylate are useful for this purpose. The functional group-containing monomer provides sites for crosslinking. The functional groups of these monomers are preferably carboxyl, hydroxy or combinations thereof. Examples of monomers that provide such groups are acrylic acid, methacrylic acid and hydroxy-containing monomers such as hydroxyethyl acrylate. The polyacrylate adhesives are preferably crosslinked using a crosslinking agent to improve their physical properties, (e.g., creek and shear resistance). The crosslinking density should be low since high degrees of crosslinking may affect the adhesive properties of the copolymer adversely. Examples of crosslinking agents are disclosed in U.S. Pat. No. 5,393,529. Solution polyacrylate pressure sensitive adhesives are commercially available under the tradenames GELVA and DURO-TAK.

Polyisobutylene (PIB) adhesives are mixtures of high molecular weight (HMW) PIB and low molecular weight (LMW) PIB. Such mixtures are described in the art. e.g., PCT/US91/02516. The molecular weight of the HMW PIB will usually be in the range of about 700,000 to 2,000,000 Da, whereas that of the LMW PIB will typically range between 35,000 to 60,000 Da. The molecular weights referred to herein are weight average molecular weight. The weight ratio of HMW PIB to LMW PIB in the adhesive will normally range between 1:1 to 2:1. The PIB adhesive will also normally include a tackifier such as polybutene oil and high Tg, low molecular weight aliphatic resins such as the ESCOREZ resins available from Exxon Chemical. Polyisobutylene adhesives are available commercially under the tradename VISTANEX from Exxon Chemical.

The silicone adhesives that may be used in forming the matrix are typically high molecular weight polydimethyl siloxanes or polydimethyldiphenyl siloxanes that contain residual silanol groups on the ends of the polymer chains. Silicone adhesives that are useful in transdermal patches are described in U.S. Pat. Nos. 5,232,702 and 4,906,169.

The polyhydric thioalcohols are preferably straight chain thioalcohols. Examples of such thioalcohols are monothioglycerol and dithioglycerol. The thioalcohol will usually constitute 0.1 to 10% by weight, more usually 0.2 to 4% by weight, of the matrix.

The aliphatic carboxylic acids that are used in combination with the thioalcohol may be straight or branched chain, saturated or have 1 to 3 sites of olefinic unsaturation, and have 0 to 2 hydroxyl groups. Examples of such acids are lauric, oleic, linoleic, myristic, palmitic, and stearic acid. Esters of such acids that may be used are preferably esters of straight or branched chain aliphatic alcohols of 1 to 14 carbon atoms and 1–2 hydroxy groups. Examples of such esters are methyl laurate, methyloleate, ethyl oleate, butyl laurate and isopropyl myristate. The acid/ester will usually constitute 0.1 to 20% by weight, more usually 0.5 to 10% by weight, of the matrix.

In addition to the pressure sensitive adhesive, sex hormone(s) and combination enhancer, the matrix may contain additives that improve adhesive or physical properties of the matrix such as hygroscopic agents that improve adhesion or silica gels that improve cold flow, antioxidants, and other additives. Preferably, the matrix is essentially free of diol.

Transdermal patches that employ the matrices of the invention will include a backing layer. The backing layer of these patches is impermeable to the drug and other components of the patch and defines the top face surface of the patch. It may be made of a single layer or film of polymer, or be a laminate of one or more polymer layers and metal foil. Examples of polymers suitable for use in making backing films are polyvinylchloride, polyvinylidene chloride, polyolefins such as polyethylene and polypropylene, polyurethane, and polyesters such as polyethylene terephthalate and ethylene-vinyl acetate copolymers.

The patches of the invention may be fabricated using procedures known in the transdermal patch art. In the case of monolith type patches, the procedure will generally involve formulating the matrix (i.e., mixing the adhesive, drug(s), enhancer and other additives, if any), casting the matrix onto the backing or release liner layer, removing solvent from the matrix and applying the backing/release liner layer as the case may be.

The following examples further illustrate the invention. These examples are not intended to limit the invention in any manner. Unless indicated otherwise, stated percentages are by weight.

EXAMPLE 1

Duro-Tak 87-2287 is a solution polyacrylate adhesive available from National Starch and Chemical Co. Its monomer composition is: vinyl acetate, 28%; 2-ethylhexyl acrylate, 67%; hydroxyethyl acrylate, 4.9% glycidal methacrylate, 0.1%. It contains no crosslinking agent. It is available as a 50% solids solution in ethyl acetate.

Mixtures of Duro-Tak 87-2287, 0.26% aluminum acetylacetonate crosslinker, 6% 17-deacetyl norgestimate (17-d-Ngm), 1% ethinyl estradiol (EE), 2% monothioglycerol (TG) and either 4% oleic acid (OA) or 10% methyl laurate (ML) were prepared. For comparison purposes, a mixture containing no enhancer was also prepared. These mixtures were cured and cast as a 100 micron thick (wet) layer onto a 3 M 1022 polyester backing and dried. Skin flux tests were carried out on the resulting assemblies according to the procedure described in col. 7 of U.S. Pat. No. 5,252,334. HPLC was used to assay for 17-d-Ngm and EE. A Perkin Elmer HPLC system with Diioderray detector set at 245 nm and 215 nm for 17-d-Ngm and EE, respectively. The mobile phase was 55% water, 45% acetonitrile at a flow rate of 1.0 ml/min. Retention time was 4.5 and 3.0 min. for 17-d-Ngm and EE, respectively. Details of the formulations and the results of the flux tests are shown in Table 1 below.

TABLE 1

| | Flux ($\mu g/cm^2/hr$) | |
|---|---|---|
| Enhancer | 17-d-Ngm | EE |
| None | 0.16 ± 0.03 | 0.033 ± 0.003 |
| TG + OA | 0.30 ± 0.04 | 0.061 ± 0.007 |
| TG + ML | 0.39 ± 0.03 | 0.076 ± 0.005 |

EXAMPLE 2

Silicone 4202 is a polydimethylsiloxane adhesive from Dow Corning. It was mixed with 4% 17-d-Ngm, 0.5% EE, 7% water soluble polyvinylpyrrolidone (K-30 from BASF; as a solution in n-propanol), 5% ML and 1% TG. This mixture is cast as a 100 micron thick (wet) layer onto a 3 M 1022 polyester backing and dried. Skin flux tests were carried out on the resulting patch as in Example 1. The 17-d-Ngm flux was 0.65±0.09 $\mu g/cm^2/hr$ and the EE flux was 0.069±0.007 $\mu g/cm^2 hr$.

EXAMPLE 3

GELVA 737 is a vinyl acetate acrylate copolymer adhesive from Monsanto. It was mixed with 0.8% estradiol (E2), 2.3% norethindrone acetate (NA), 1.1% silica gel (SG), 0.8% OA, and 0.4% TG in Gelva 737. For comparison purposes, a blend containing no enhancer was also prepared. The mixtures were blended thoroughly and cast onto a Saranex backing at a thickness of 15 mil (wet) and dried at 70° C. Flux studies were carried out as in Example 1. The results of these studies are reported in Table 2 below.

TABLE 2

| | Flux ($\mu g/cm^2/hr$) | |
|---|---|---|
| Formulation | E2 | NA |
| No Enhancer | 0.16 ± 0.013 | 0.17 ± 0.009 |
| Enhancer + SG | 0.27 ± 0.015 | 0.37 ± 0.042 |

Modifications of the above described modes for carrying out the invention that are obvious to persons of skill in the transdermal patch art are intended to be within the scope of the following claims.

We claim:

1. A matrix for use in transdermally administering a sex steroid consisting essentially of a mixture of
   a) a pressure-sensitive adhesive;
   b) a sex steroid; and
   c) a skin permeation enhancer consisting essentially of a mixture of:
      (i) a polyhydric thioalcohol of 2 to 6 carbon atoms having at least one mercapto group and at least one hydroxy group; and
      (ii) an aliphatic carboxylic acid of 8 to 24 carbon atoms or an ester of said acid.

2. The matrix of claim 1 wherein the sex steroid is an estrogen, a progestogen or a combination of an estrogen and a progestogen.

3. The matrix of claim 1 wherein the ester is an ester of said acid and an aliphatic alcohol of 1 to 14 carbon atoms and 1 to 2 hydroxy groups.

4. The matrix of claim 1 wherein the pressure sensitive adhesive is a solution of a polyacrylate, a polyisobutylene, a silicone, or a styrene copolymer.

5. The matrix of claim 2 wherein the polyhydric thioalcohol is a thioglycerol.

6. The matrix of claim 1 wherein the thioglycerol is monothioglycerol.

7. The matrix of claim 1 wherein the pressure sensitive adhesive is a solution polyacrylate, a silicone, or a polyisobutylene adhesive, the sex steroid is a combination of at least one estrogen and at least one progestogen, the thioalcohol is monothioglycerol, the acid is oleic acid and the ester is methyl laurate.

8. A transdermal patch for administering a sex steroid comprising a laminated composite of:
   a) a backing layer; and
   b) a layer of the matrix of claim 2 underlying the backing layer.

9. A transdermal patch for administering a sex steroid comprising a laminated composite of:
   a) a backing layer; and
   b) a layer of the matrix of claim 2 underlying the backing layer.

10. A transdermal patch for administering a sex steroid comprising a laminated composite of:
    a) a backing layer; and
    b) a layer of the matrix of claim 3 underlying the backing layer.

11. A transdermal patch for administering a sex steroid comprising a laminated composite of:
    a) a backing layer; and
    b) a layer of the matrix of claim 4 underlying the backing layer.

12. A transdermal patch for administering a sex steroid comprising a laminated composite of:
    a) a backing layer; and
    b) a layer of the matrix of claim 5 underlying the backing layer.

13. A transdermal patch for administering a sex steroid comprising a laminated composite of:
    a) a backing layer; and
    b) a layer of the matrix of claim 6 underlying the backing layer.

14. A transdermal patch for administering a sex steroid comprising a laminated composite of:
    a) a backing layer; and
    b) a layer of the matrix of claim 7 underlying the backing layer.

* * * * *

UNITED STATES PATENT AND TRADEMARK OFFICE
CERTIFICATE OF CORRECTION

PATENT NO. : 5,693,335
DATED : December 2, 1997
INVENTOR(S) : Jun Xia, Janan Jona and Chia-Ming Chiang It is certified that error appears in the above-identified patent and that said Letters Patent is hereby corrected as shown below:

On the title page:

In the References Cited, ref. 3, "Chien" should be --Chien et al.--

Column 4, line 11, delete the space between "3 M"
        line 15, "Diioderray" should be --Diiodearray--
        line 38, delete the space between "3 M"

Column 5, line 22, "2" should be --1--

Column 6, line 1, "2" should be --1--

Signed and Sealed this

Twenty-fourth Day of February, 1998

Attest:

BRUCE LEHMAN

Attesting Officer        Commissioner of Patents and Trademarks